(12) United States Patent
Liptak et al.

(10) Patent No.: US 12,722,161 B2
(45) Date of Patent: Sep. 1, 2026

(54) ION GENERATOR AND SYSTEM WITH MOBILE HVAC

(71) Applicant: Dometic Sweden AB, Solna (SE)

(72) Inventors: William Joseph Liptak, Pompano Beach, FL (US); Charlie Alvin Barefoot, Jr., Dinwiddie, VA (US); Benjamin John Haynes, Jr., Middleburg, FL (US)

(73) Assignee: Dometic Sweden AB, Solna (SE)

( * ) Notice: Subject to any disclaimer, the term of this patent is extended or adjusted under 35 U.S.C. 154(b) by 441 days.

(21) Appl. No.: 17/884,135

(22) Filed: Aug. 9, 2022

(65) Prior Publication Data

US 2023/0048412 A1 Feb. 16, 2023

Related U.S. Application Data

(60) Provisional application No. 63/232,368, filed on Aug. 12, 2021.

(51) Int. Cl.

| | |
|---|---|
| ***B03C 3/38*** | (2006.01) |
| ***A61L 9/22*** | (2006.01) |
| ***B03C 3/36*** | (2006.01) |
| ***B03C 3/68*** | (2006.01) |
| ***F24F 8/30*** | (2021.01) |
| ***H01T 23/00*** | (2006.01) |

(52) U.S. Cl.

CPC .................. *B03C 3/38* (2013.01); *A61L 9/22* (2013.01); *B03C 3/368* (2013.01); *B03C 3/68* (2013.01); *F24F 8/30* (2021.01); *H01T 23/00* (2013.01); *A61L 2209/16* (2013.01); *B03C 2201/30* (2013.01)

(58) Field of Classification Search

CPC combination set(s) only.
See application file for complete search history.

(56) References Cited

U.S. PATENT DOCUMENTS

| | | | |
|---|---|---|---|
| D205,975 | S | 10/1966 | Sato et al. |
| 3,444,854 | A | 5/1969 | Fraim |
| 3,724,442 | A | 4/1973 | Gurney |
| 3,727,537 | A | 4/1973 | Harty |
| D284,025 | S | 5/1986 | Armstrong |

(Continued)

FOREIGN PATENT DOCUMENTS

| | | |
|---|---|---|
| AT | 168943 | 8/1998 |
| AT | 346760 | 12/2006 |

(Continued)

OTHER PUBLICATIONS

International Report on Patentability issued in PCT Application No. PCT/IB2022/057429 mailed on Feb. 22, 2024.

(Continued)

*Primary Examiner* — Jennifer Dieterle
*Assistant Examiner* — Sonji Turner
(74) *Attorney, Agent, or Firm* — Dinsmore & Shohl LLP

(57) ABSTRACT

Present embodiments relate to ionization of air flow within heating, ventilation and air conditioning (HVAC) systems. More specifically, but without limitation, present embodiments relate to ionization systems, for example bipolar ionization, which are controlled in part by a signal from or powered by the blower motor controller of the HVAC system so that the ionization system functions when the blower is on.

15 Claims, 8 Drawing Sheets

(56) References Cited

U.S. PATENT DOCUMENTS 4,641,502 A 2/1987 Aldrich et al.
4,672,818 A 6/1987 Roth
4,689,715 A * 8/1987 Halleck .................... H05F 3/04 361/231
D306,341 S 2/1990 Bales et al.
D309,288 S 7/1990 Haverly
5,055,963 A * 10/1991 Partridge ................ H01T 23/00 361/231
5,062,351 A 11/1991 Kloster
5,116,280 A 5/1992 Kloster
5,531,641 A 7/1996 Aldrich
D376,640 S 12/1996 Kloster
5,899,081 A 5/1999 Evans et al.
6,116,095 A 9/2000 Radle
6,213,197 B1 4/2001 Ebbeson
6,263,689 B1 7/2001 Dodge et al.
6,449,973 B2 9/2002 Dodge et al.
6,464,000 B1 10/2002 Kloster
6,471,752 B1 * 10/2002 Lewis ...................... B03C 3/68 96/97
6,719,207 B2 4/2004 Kloster
D490,374 S 5/2004 Amakawa et al.
6,857,953 B2 2/2005 Malott
D513,070 S 12/2005 Haranaka
6,978,630 B2 12/2005 Wensink et al.
6,987,792 B2 1/2006 Do et al.
7,065,981 B2 6/2006 Ebbeson
7,140,192 B2 11/2006 Allen et al.
7,171,822 B2 2/2007 Allen et al.
7,234,315 B2 6/2007 Allen et al.
7,237,397 B2 7/2007 Allen
7,316,119 B2 1/2008 Allen
D574,323 S 8/2008 Waaler
7,419,368 B2 9/2008 Milks
7,846,227 B2 * 12/2010 Gotoh ...................... A61L 9/22 361/231
7,963,117 B2 6/2011 Allen et al.
8,056,351 B2 11/2011 Marciano et al.
8,056,933 B2 11/2011 Liptak
8,149,561 B2 4/2012 Shimanaka
D662,055 S 6/2012 Little et al.
8,240,168 B2 8/2012 Holguin
8,440,143 B2 5/2013 Liptak
8,535,127 B2 9/2013 Malott
8,540,509 B1 9/2013 Cantal
8,564,924 B1 10/2013 Waddell
8,568,209 B2 10/2013 Boxum
D696,196 S 12/2013 Plato et al.
8,861,167 B2 10/2014 Waddell
8,861,168 B2 10/2014 Waddell
8,873,215 B2 10/2014 Waddell
9,025,303 B2 5/2015 Waddell
9,168,538 B2 10/2015 Waddell
9,289,779 B2 3/2016 Waddell
D753,614 S 4/2016 Xiang et al.
D762,289 S 7/2016 Schmidt et al.
D764,034 S 8/2016 Schmidt et al.
D764,035 S 8/2016 Schmidt et al.
9,441,845 B2 9/2016 Waddell
9,478,948 B2 10/2016 Waddell
9,509,125 B2 11/2016 Waddell
9,551,497 B2 1/2017 Waddell
9,610,824 B2 4/2017 Allen et al.
9,631,832 B2 4/2017 Malott
D785,771 S 5/2017 Bergin
D785,772 S 5/2017 Bergin
9,660,425 B1 5/2017 Sunshine
9,834,062 B2 12/2017 Esch
9,839,714 B2 12/2017 Waddell
9,847,623 B2 12/2017 Sunshine
9,849,208 B2 12/2017 Waddell
D811,566 S 2/2018 Liu et al.
9,925,292 B2 3/2018 Waddell
9,925,567 B2 3/2018 Waddell
D817,466 S 5/2018 Moseley
9,975,405 B2 5/2018 Siddiqui et al.
9,985,421 B2 5/2018 Sunshine
D824,499 S 7/2018 Williamson et al.
10,014,667 B2 7/2018 Sunshine
10,020,180 B2 7/2018 Waddell
10,073,055 B2 9/2018 Waddell
10,093,152 B2 10/2018 Allard et al.
10,107,520 B2 10/2018 Schmidt et al.
10,111,978 B2 10/2018 Waddell
D832,987 S 11/2018 Bergin
10,128,075 B2 11/2018 Waddell
10,153,623 B2 12/2018 Sunshine
D840,932 S 2/2019 Markoski et al.
D841,138 S 2/2019 Williamson et al.
10,297,984 B2 5/2019 Sunshine
D850,609 S 6/2019 Bergin
10,317,096 B2 6/2019 Waddell
10,319,569 B2 6/2019 Waddell
10,322,205 B2 6/2019 Waddell
10,383,970 B2 8/2019 Waddell
D862,668 S 10/2019 Moseley
10,439,370 B2 10/2019 Sunshine
D865,926 S 11/2019 Moseley
10,508,867 B2 12/2019 Dowell, Jr. et al.
D875,046 S 2/2020 Waddell
10,566,769 B2 2/2020 Waddell
10,589,593 B2 3/2020 Fedor et al.
D884,870 S 5/2020 Bergin
D887,982 S 6/2020 Schmidt
10,695,455 B2 6/2020 Waddell
10,696,129 B2 6/2020 Bergin
10,710,123 B2 7/2020 Waddell
D899,560 S 10/2020 Kawasaki et al.
D905,217 S 12/2020 Hederstierna et al.
D907,183 S 1/2021 Meda et al.
D915,569 S 4/2021 Meda et al.
D917,036 S 4/2021 Hederstierna et al.
10,978,858 B2 4/2021 Sunshine
10,980,911 B2 4/2021 Waddell
11,018,478 B2 5/2021 Sunshine
11,027,595 B2 6/2021 Smith et al.
11,034,208 B2 6/2021 Williamson et al.
D940,289 S 1/2022 Hederstierna et al.
D944,374 S 2/2022 Hederstierna et al.
11,247,537 B2 2/2022 Chevalier
11,254,183 B2 2/2022 Peter et al.
D956,940 S 7/2022 Meda et al.
11,376,925 B2 7/2022 Williamson et al.
11,472,256 B2 10/2022 Williamson et al.
11,491,496 B1 * 11/2022 Galbreath ............. B64D 13/06
11,511,603 B2 11/2022 Bilston et al.
11,560,036 B2 1/2023 Williamson et al.
11,571,945 B2 2/2023 Liu et al.
11,613,157 B2 3/2023 Fedor et al.
D996,367 S 8/2023 Muthu et al.
D999,739 S 9/2023 Muthu et al.
11,752,827 B2 9/2023 Meda et al.
2002/0071235 A1 * 6/2002 Gorczyca ................ H01T 23/00 361/231
2003/0098650 A1 * 5/2003 Adachi ................... H01T 23/00 313/587
2005/0031503 A1 * 2/2005 Fox ......................... F24F 8/192 422/186.04
2005/0160709 A1 7/2005 Hollis
2005/0231884 A1 * 10/2005 Miyaishi ................... B03C 3/32 361/231
2006/0052050 A1 3/2006 Malott et al.
2007/0221370 A1 9/2007 Allen et al.
2007/0227693 A1 10/2007 Allen et al.
2009/0042502 A1 * 2/2009 Kim ..................... B60H 3/0078 361/231
2009/0209193 A1 8/2009 Kloster et al.
2010/0027186 A1 * 2/2010 Chang ..................... H01T 23/00 361/230
2011/0165018 A1 7/2011 Lynn
2013/0232807 A1 9/2013 Robert et al.
2014/0306608 A1 * 10/2014 Nagatome ............... H01J 27/26 315/111.81

(56) References Cited

U.S. PATENT DOCUMENTS

| | | | | |
|---|---|---|---|---|
| 2015/0083931 | A1* | 3/2015 | Temporin | H01T 23/00 250/426 |
| 2015/0165084 | A1 | 6/2015 | Waddell | |
| 2016/0204581 | A1* | 7/2016 | Nishida | H01T 23/00 250/423 F |
| 2016/0218490 | A1 | 7/2016 | Nishida et al. | |
| 2016/0221002 | A1 | 8/2016 | Lin et al. | |
| 2019/0047353 | A1 | 2/2019 | Williamson et al. | |
| 2019/0247862 | A1* | 8/2019 | Galbreath | B64D 13/06 |
| 2019/0247893 | A1 | 8/2019 | Waddell | |
| 2019/0328923 | A1 | 10/2019 | Cunningham | |
| 2020/0039325 | A1 | 2/2020 | Jensen | |
| 2020/0062622 | A1 | 2/2020 | Linley et al. | |
| 2020/0338951 | A1 | 10/2020 | Paci et al. | |
| 2020/0338958 | A1 | 10/2020 | Lundqvist | |
| 2020/0340679 | A1 | 10/2020 | Waddell | |
| 2020/0388994 | A1 | 12/2020 | Waddell | |
| 2021/0061058 | A1 | 3/2021 | Meda et al. | |
| 2021/0061060 | A1 | 3/2021 | Meda et al. | |
| 2021/0196853 | A1 | 7/2021 | Waddell | |
| 2021/0197208 | A1 | 7/2021 | Sunshine | |
| 2021/0207882 | A1 | 7/2021 | Jurek | |
| 2021/0276396 | A1 | 9/2021 | Jurek | |
| 2022/0001718 | A1 | 1/2022 | Jurek | |
| 2022/0009306 | A1 | 1/2022 | Hornung | |
| 2022/0063369 | A1 | 3/2022 | Chen et al. | |
| 2022/0169090 | A1 | 6/2022 | Peter et al. | |
| 2022/0176775 | A1 | 6/2022 | Jurek et al. | |
| 2022/0227200 | A1 | 7/2022 | Hildebrand | |
| 2022/0332170 | A1 | 10/2022 | Williamson et al. | |
| 2023/0048412 | A1 | 2/2023 | Liptak et al. | |
| 2023/0136360 | A1 | 5/2023 | Strang et al. | |
| 2023/0138744 | A1 | 5/2023 | Strang et al. | |
| 2023/0166576 | A1 | 6/2023 | Liu et al. | |
| 2023/0182528 | A1 | 6/2023 | Strang et al. | |
| 2023/0226879 | A1 | 7/2023 | Fedor et al. | |
| 2023/0226880 | A1 | 7/2023 | Fedor et al. | |
| 2023/0226881 | A1 | 7/2023 | Chen et al. | |
| 2023/0366580 | A1* | 11/2023 | Bowman | F24F 11/63 |

FOREIGN PATENT DOCUMENTS

| | | | | | |
|---|---|---|---|---|---|
| AT | 352442 | | 2/2007 | | |
| AT | 419984 | | 1/2009 | | |
| AU | 7615898 | | 1/1999 | | |
| AU | 2004202967 | | 6/2005 | | |
| AU | 2005209633 | | 3/2006 | | |
| AU | 2007202766 | | 1/2008 | | |
| AU | 2007237183 | | 6/2008 | | |
| AU | 2008288394 | | 2/2009 | | |
| AU | 2009233601 | | 6/2010 | | |
| AU | 2012261549 | | 1/2013 | | |
| AU | 354553 | S | 3/2014 | | |
| AU | 360022 | S | 1/2015 | | |
| AU | 360131 | S | 1/2015 | | |
| AU | 360132 | S | 1/2015 | | |
| AU | 367405 | S | 3/2016 | | |
| AU | 201612249 | S | 5/2016 | | |
| AU | 201613590 | S | 7/2016 | | |
| AU | 201613591 | S | 7/2016 | | |
| AU | 201613592 | S | 7/2016 | | |
| AU | 201613593 | S | 7/2016 | | |
| AU | 2015226832 | | 9/2016 | | |
| AU | 2016101949 | | 12/2016 | | |
| AU | 2015289763 | | 1/2017 | | |
| AU | 2017100215 | | 3/2017 | | |
| AU | 201712794 | S | 5/2017 | | |
| AU | 201712798 | S | 5/2017 | | |
| AU | 2017200186 | | 8/2017 | | |
| AU | 20180977 | S | 3/2018 | | |
| AU | 201810968 | S | 3/2018 | | |
| AU | 201810969 | S | 3/2018 | | |
| AU | 201810970 | S | 3/2018 | | |
| AU | 201810971 | S | 3/2018 | | |
| AU | 201810972 | S | 3/2018 | | |
| AU | 201810973 | S | 3/2018 | | |
| AU | 201810975 | S | 3/2018 | | |
| AU | 201810978 | S | 3/2018 | | |
| AU | 2017222698 | | 8/2018 | | |
| AU | 2017227050 | | 8/2018 | | |
| AU | 2017222697 | | 9/2018 | | |
| AU | 201816419 | S | 1/2019 | | |
| AU | 2017364256 | | 6/2019 | | |
| AU | 2018232195 | | 10/2019 | | |
| AU | 2019202512 | | 10/2019 | | |
| AU | 2018366469 | | 5/2020 | | |
| AU | 2017101887 | | 10/2020 | | |
| AU | 2019291452 | | 1/2021 | | |
| AU | 2020212092 | | 7/2021 | | |
| AU | 2020365568 | | 4/2022 | | |
| AU | 2021239071 | | 7/2022 | | |
| AU | 2022228161 | | 9/2022 | | |
| AU | 2021237758 | | 10/2022 | | |
| AU | 2021238656 | | 10/2022 | | |
| AU | 2021238665 | | 10/2022 | | |
| AU | 2021269719 | | 10/2022 | | |
| AU | 2021272270 | | 10/2022 | | |
| AU | 2021272652 | | 10/2022 | | |
| AU | 2022202525 | | 11/2022 | | |
| AU | 2023202002 | | 5/2023 | | |
| CA | 2500515 | | 9/2005 | | |
| CA | 2500516 | | 9/2005 | | |
| CA | 2500519 | | 9/2005 | | |
| CA | 2500790 | | 9/2005 | | |
| CA | 2518348 | | 3/2006 | | |
| CA | 2587994 | | 12/2007 | | |
| CA | 2611822 | | 5/2008 | | |
| CA | 2686403 | | 5/2010 | | |
| CA | 2906348 | | 9/2014 | | |
| CA | 2954152 | | 1/2016 | | |
| CA | 160490 | S | 3/2016 | | |
| CA | 166803 | S | 3/2016 | | |
| CA | 166804 | S | 3/2016 | | |
| CA | 165232 | S | 5/2016 | | |
| CA | 165233 | S | 5/2016 | | |
| CA | 167431 | S | 2/2017 | | |
| CA | 172872 | S | 2/2017 | | |
| CA | 172873 | S | 2/2017 | | |
| CA | 172874 | S | 2/2017 | | |
| CA | 3019194 | | 10/2017 | | |
| CA | 174116 | S | 2/2018 | | |
| CA | 179097 | S | 2/2018 | | |
| CA | 2981668 | A1 | 4/2018 | | |
| CA | 3055636 | A1 | 9/2018 | | |
| CA | 2951956 | | 3/2022 | | |
| CN | 1842684 | | 10/2006 | | |
| CN | 102725155 | | 10/2012 | | |
| CN | 106470856 | | 3/2017 | | |
| CN | 304097003 | | 4/2017 | | |
| CN | 106976376 | | 7/2017 | | |
| CN | 304288703 | S | 9/2017 | | |
| CN | 304888719 | S | 11/2018 | | |
| CN | 109070688 | S | 12/2018 | | |
| CN | 305029216 | S | 2/2019 | | |
| CN | 305029217 | S | 2/2019 | | |
| CN | 305029218 | S | 2/2019 | | |
| CN | 305105066 | S | 4/2019 | | |
| CN | 110385958 | A | 10/2019 | | |
| CN | 305397384 | S | 10/2019 | | |
| CN | 110520314 | A | 11/2019 | | |
| CN | 209888586 | | 1/2020 | | |
| CN | 110753440 | A * | 2/2020 | | H02P 29/00 |
| CN | 210082872 | | 2/2020 | | |
| CN | 210118942 | | 2/2020 | | |
| CN | 111271997 | | 6/2020 | | |
| CN | 111344168 | | 6/2020 | | |
| CN | 111442670 | | 7/2020 | | |
| CN | 306092208 | | 10/2020 | | |
| CN | 112203881 | | 1/2021 | | |
| CN | 112384387 | | 2/2021 | | |
| CN | 213237518 | | 5/2021 | | |
| CN | 213237945 | | 5/2021 | | |
| CN | 306672354 | S | 7/2021 | | |

(56) References Cited

FOREIGN PATENT DOCUMENTS

CN 306681352 S 7/2021
CN 306901266 S 10/2021
CN 215244234 12/2021
CN 114585528 6/2022
CN 307425658 S 6/2022
CN 307425659 S 6/2022
CN 217022121 7/2022
CN 307449465 S 7/2022
CN 115214301 10/2022
CN 115280069 11/2022
CN 115280070 11/2022
CN 115298480 11/2022
CN 115515807 12/2022
CN 115551727 A 12/2022
CN 115605361 1/2023
CN 115703320 2/2023
DE 2217596 10/1972
DE 19730136 1/1999
DE 10209837 A1 * 9/2003 ......... B60H 1/00507
DE 10336767 12/2004
DE 59812376 1/2005
DE 202004017266 4/2006
DE 202005000560 6/2006
DE 602004004480 3/2007
DE 202006009803 12/2007
DE 602005008048 8/2008
DE 102007038716 2/2009
DE 602005012194 2/2009
DE 102008028066 12/2009
DE 102016220768 4/2018
DE 102016223050 5/2018
DE 112017000915 10/2018
DE 102017214941 2/2019
DE 102017207797 8/2019
DE 102018206490 10/2019
DE 102019205194 10/2019
DE 102018206854 11/2019
DE 112018003284 3/2020
DE 202015009786 3/2020
DE 212018000248 3/2020
DE 212018000249 3/2020
DE 112018003288 4/2020
DE 102018222877 6/2020
DE 112018005883 7/2020
DE 102019205908 10/2020
DE 112019002266 1/2021
DE 102020209854 2/2021
DE 102019212946 3/2021
DE 102019212947 3/2021
DE 102019212949 3/2021
DE 102020203424 7/2021
DE 102020203422 9/2021
DE 102020203423 9/2021
DE 112020000265 9/2021
DE 102020206181 11/2021
DE 102020206182 11/2021
DE 102020206183 11/2021
DE 112020001585 12/2021
DE 102020208653 1/2022
DE 112020004382 6/2022
DE 102021200499 7/2022
DE 102022203759 10/2022
DE 112021000525 12/2022
DE 102021208289 2/2023
DE 102023200320 7/2023
DK 700801 2/1999
DK 200600972 2/2007
DK 1538009 4/2007
DK 1634740 4/2009
DK 1870270 3/2012
EP 700801 7/1998
EP 869018 1/1999
EP 892225 12/2004
EP 1506886 11/2006
EP 1721765 11/2006
EP 1538009 1/2007
EP 1925889 5/2008
EP 1752717 7/2008
EP 1634740 1/2009
EP 2189312 5/2010
EP 1870270 11/2011
EP 2433658 10/2015
EP 2178710 11/2015
EP 2192040 11/2015
EP 2196390 11/2015
EP 1955946 3/2017
EP 3113965 10/2017
EP 3303965 4/2018
EP 3401619 11/2018
EP 3564564 11/2019
EP 3241695 6/2020
EP 3411250 10/2020
EP 3797042 3/2021
EP 3436752 6/2021
EP 3592585 7/2021
EP 3910261 11/2021
EP 4121692 1/2023
EP 4121693 1/2023
EP 4121694 1/2023
ES 2119272 10/1998
ES 2557428 1/2016
FI 7327 12/2006
IT 201700090904 2/2019
IT 201700090907 2/2019
IT 201900014247 2/2021
IT 201900019193 4/2021
JP H11118229 A * 4/1999 .............. F24F 13/20
KR 20080004918 U * 10/2008 ............... A61L 9/22
MX 343494 11/2016
MX 354798 3/2018
PL 382714 12/2007
PL 2504183 4/2018
RU 2753994 8/2021
SE 601741 2/2007
SI 22290 12/2007
WO WO2006021226 3/2006
WO 2007078135 A1 7/2007
WO WO2009021994 2/2009
WO WO2011063961 6/2011
WO WO2014143181 9/2014
WO WO2016011073 1/2016
WO WO2016189520 12/2016
WO WO2017143393 8/2017
WO WO2017143394 8/2017
WO WO2017149442 9/2017
WO WO2018096127 5/2018
WO WO2019025633 2/2019
WO WO2019025634 2/2019
WO WO2019025635 2/2019
WO WO2019025636 2/2019
WO WO2019038023 2/2019
WO WO2019097448 5/2019
WO WO2019229706 12/2019
WO WO2019244011 12/2019
WO WO2020114443 6/2020
WO WO2020151541 7/2020
WO WO2020188485 9/2020
WO WO2020192746 10/2020
WO WO2021074841 4/2021
WO WO2021185903 9/2021
WO WO2021185906 9/2021
WO WO2021185918 9/2021
WO WO2021186414 9/2021
WO WO2021228601 11/2021
WO WO2021228605 11/2021
WO WO2021228620 11/2021
WO WO2022162534 8/2022
WO WO2023006307 2/2023

(56) References Cited

FOREIGN PATENT DOCUMENTS

| | | |
|---|---|---|
| WO | WO2023011534 | 2/2023 |
| WO | WO2023017422 | 2/2023 |

OTHER PUBLICATIONS

European Patent Application No. 22761611.7 Ion Generator for HVAC System Application filed on Feb. 20, 2024.
Notice of Allowance issued in U.S. Appl. No. 29/803,390 mailed on Jan. 25, 2023.
Notice of Allowance issued in U.S. Appl. No. 29/816,164 mailed on Mar. 31, 2023.
Supplemental Notice of Allowability issued in U.S. Appl. No. 29/816,164 mailed on Apr. 18, 2023.
Notice of Allowability issued in U.S. Appl. No. 29/803,390 mailed on May 5, 2023.
Supplemental Notice of Allowability issued in U.S. Appl. No. 29/816,164 mailed on May 31, 2023.
Registration Certificate issued in United Kingdom Application No. 6191421 mailed on Feb. 11, 2022.
Registration Certificate issued in United Kingdom Application No. 6191422 mailed on Feb. 11, 2022.
Registration Certificate issued in United Kingdom Application No. 6191423 mailed on Feb. 11, 2022.
Notification of Registration issued in European Union Application No. 008858435-0001-0003 mailed on Feb. 18, 2022.
PCT Application No. PCT/IB2022/057429 titled "Ion Generator for HVAC System Application" filed on Aug. 9, 2022.
International Search Report and Written opinion issued in PCT Application No. PCT/IB2022/057429 mailed on Nov. 18, 2022.
10-Minute Tech, Trailer Life, Jul. 1996, pp. 69-70 dated Jul. 1, 1996.
American RV Company, Dometic 459530 Duo Therm 13,500 BTU Brisk Air Conditioner High Efficiency Upper Unit Trailer Camper RV, Mar. 23, 2014, https://web.archive.org/web/20140323013456/ http://www.americanrvcompany.com/Dometic-459530-Duo-Therm-13500-BTU-Brisk-Air-Conditioner-High-Efficiency-Upper-Unit-Trailer-Camper-RV Mar. 23, 2014.
American RV Company, Dometic 541815 High Performance 13,500 BTU Air Conditioner Upper Unit CCC2 Required Electronics Pre-Installed Camper Trailer RV, https://web.archive.org/web/20140323014940/http://www.americanrvcompany.com/Dometic-541815-High-Performance-13500-BTU-Air-Conditioner-Upper-Unit-CCC2-Required-Electronics-Pre-Installed-Camper-Trailer-RV Mar. 23, 2014.
American RV Company, Dometic 541916 High Performance 15,000 BTU Air Conditioner Upper Unit Single Zone LCD Thermostat Required Electronics Pre-Installed Camper Trailer RV, https://web.archive.org/web/20140323014952/ http://www.americanrvcompany.com/Dometic-541916-High-Performance-15000-BTU-Air-Conditioner-Upper-Unit-Single-Zone-LCD-Thermostat-Required-Electronics-Pre-Installed-Camper-Trailer-RV Mar. 23, 2014.
American RV Company, Dometic 551816 High Performance 15,000 BTU Heat Pump for Comfort Control Center II Camper Trailer RV, http://www.americanrvcompany.com/Dometic-551816-High-Performance-15000-BTU-Heat-Pump-for-Comfort-Control-Center-II-Camper-Trailer-RV Apr. 15, 2012.
American RV Company, Dometic 541816 High Performance 15,000 BTU Air Conditioner Upper Unit CCC2 Required Electronics Pre-Installed Camper Trailer RV, http://www.americanrvcompany.com/Dometic-541816-High-Performance-15000-BTU-Air-Conditioner-Upper-Unit-CCC2-Required-Electronics-Pre-Installed-Camper-Trailer-RV Mar. 23, 2014.
Dirna Bergstrom: Slim Cool; http://www.dirna.com/files/dirna-manuals/220RE00183.pdf May 21, 2014.
Dometic Corporation, Dometic High Performance Air Conditioners, 2 pages, Jan. 1, 2011.
Dometic Duo-Therm, p. 140, Feb. 23, 2013.
Dometic Group: "Climate Control", http://www.dometic.com/enus/Americas/USA/RV-Products/climate, 2 pages.
DOMETIC Waeco Coolair RT 880; http://vwww.dometic.co.uk/product/waeco-coolair-rt-880-2/ May 14, 2015.
Eberspacher Cooltronic Parking Coolers with High Efficiency with the Engine Off; http://www.eberspacher.com/products/air-conditioning/cooltronic-truck-parking-coolers.html Jun. 23, 2015.
Indelb; WO Oblo; Sleeping Well Oblo; http://www.indelb.com/products/parking_air_cooler/sleeping_well/sw_oblo Apr. 1, 2016.
Webasto: Rooftop air conditioning systems: Rooftop 3.5-9.9 kw; https://web.archive.org/web/20161201014045/ https://www.webasto.com/au/markets-products/off-highway/air-conditioning/rooftop-air-conditioning/rooftop-ac-35-99-kw/.
Webasto; Truck parking cooler: Cool Top Vario 10 E; http://www.webasto.com/GB/marketsproducts/truck/air-conditioning/products/cool-top-vario/ Apr. 25, 2016.
Youtube; Viesa Kompressor; https://www.youtube.com/watch?v=SPK17XEvVLO May 22, 2012 (https://www.google.com/?gws_rd=ssl#q=https://www.youtube.com/watch?v%3DSPK17XEvVL0&spf=1495819902591).
Dirna Bergstrom: Parking Coolers—No-Idle Electrical A/C—MiniCool Compact 1.4; http://www.dirna.com/parking-coolers-no-idle-electrical-ac-compact/ Mar. 17, 2015.
Dometic Catalog—Climate Control Products—2015.
Dometic Catalog—Climate Control Products—2016.
U.S. Appl. No. 18/449,354, filed Aug. 14, 2023 titled Air Distribution Apparatus.
Design U.S. Appl. No. 29/915,483, filed Oct. 31, 2023 titled Air Distribution Box.
Australian Patent Application No. 2022326879 titled "Ion Generator for HVAC System Application" filed on Feb. 13, 2024.
Plasma Air; Plasma Air's Needlepoint Bipolar Ionization Technology Passes, 1 page, Aug. 5, 2020.
GPS; Third-Party Testing, Needlepoint Bipolar Ionization Test Results, 10 pages, Jul. 21, 2021.
AtmosAir; About—Certifications—AtmosAir; 2 pages, Jul. 20, 2021.
Nu-Calgon; iWave-R Air Purifier, 6 pages, Jul. 22, 2021.
Shanghai Zeluo Electronic Technology Co., Ltd., Trumpxp; Product Center—Air Purifier, Retrieved from Internet Wayback Machine on Mar. 30, 2022, but first published Feb. 23, 2013.
U.S. Appl. No. 63/232,368 entitled "Ion Generator and System with Mobile HVAC", filed Aug. 12, 2021.
Design U.S. Appl. No. 29/803,390 entitled "Housing for an Ion Generator", filed Aug. 12, 2021.
Design U.S. Appl. No. 29/816,164 entitled "Housing for an Ion Generator", filed Nov. 19, 2021.
European Union Application No. 008858435-0001-0003 titled "Housing for an Ion Generator" filed on Feb. 11, 2022.
United Kingdom Application No. 6191421 titled "Housing for an Ion Generator" filed on Feb. 11, 2022.
United Kingdom Application No. 6191422 titled "Housing for an Ion Generator" filed on Feb. 11, 2022.
United Kingdom Application No. 6191423 titled "Housing for an Ion Generator" filed on Feb. 11, 2022.

* cited by examiner

ION GENERATOR AND SYSTEM WITH MOBILE HVAC

CLAIM TO PRIORITY

This non-provisional patent application claims priority to and benefit of, under 35 U.S.C. § 119(e), U.S. Provisional Patent Application Ser. No. 63/232,368, filed Aug. 12, 2021 and titled "Ion Generator and System with Mobile HVAC", all of which is incorporated by reference herein.

BACKGROUND

1. Field of the Invention

Present embodiments relate to ionization of air flow within heating, ventilation and air conditioning (HVAC) systems. More specifically, but without limitation, present embodiments relate to ionization systems, for example bipolar ionization, which are controlled in part by a signal from or powered by the blower motor controller of the HVAC system so that the ionization system functions when the blower is on.

2. Description of the Related Art

Air is commonly treated to clean the air and reduce pollutants and contaminants. For example, in heating, ventilation and air-conditioning (HVAC) applications, air may be heated, cooled, humidified, dehumidified, filtered or otherwise treated for delivery into residential, commercial or other environmentally controlled spaces.

Ion generation may be performed to ionize the air and improve the treatment and filter of the air. It may be desirable to utilize ion generation on mobile HVAC, for example recreational vehicles and marine vehicles or crafts.

Further however, ionization is improved if airflow is moving over the electrodes or emitters. However, continuous power or function of an ionizer may result in operation during a period of time when the HVAC is not operating.

The information included in this Background section of the specification, including any references cited herein and any description or discussion thereof, is included for technical reference purposes only and is not to be regarded subject matter by which the scope of the invention is to be bound.

SUMMARY

The present embodiments provide an ion generator and arrangement for mounting same to mobile HVAC systems so that air may be better cleaned, filtered, and/or purified in mobile applications. Present embodiments provide an ion generator that is capable of being mounted on mobile HVAC systems utilized in RV and marine vehicles or crafts, and which are powered for operation when a blower motor is operating, so that maximum efficiency of ionization is provided.

According to some embodiments an ion generator may comprise a housing assembly having at least one housing, a first wire extending from the housing assembly and a second wire extending from the housing assembly. The housing assembly may have a potted ion generator module therein to create ions and in electrical communication with the first wire and the second wire. A first emitter may be located at an end of the first wire and a second emitter located at an end of the second wire, each of the ends having a brush. The ion generator may further comprise a connector which extends from the housing assembly, the connector capable of receiving power from a blower motor controller, of a mobile HVAC so that the ion generator operates when one of the blower motor or the blower motor controller is operating.

In some optional embodiments, the following features may be utilized alone in combination with the ion generator or in combination with other features and the ion generator. The ion generator may further comprise first and second grommets, wherein the first wire and the second wire extend through each of the first and second grommets, respectively. The mobile HVAC may be a marine HVAC system. The marine HVAC system may comprise an air handler housing. The blower housing having first and second holes which receive the first and second grommets respectively of the first wire and the second wire. The ion generator may further comprise a printed circuit board which receives a power input from the blower motor controller and outputs DC power to the ion generator. The mobile HVAC may also being a recreational vehicle (RV) HVAC system. The RV HVAC system may have an enclosure. The first and second grommets and the first wire and the second wire may be disposed in the enclosure. The ion generator may further comprise a printed circuit board which receives a power input from the blower motor controller and outputs DC power to the ion generator. The ion generator may further comprise a light to indicate power on the housing assembly.

According to some embodiments, a bipolar ionization system may comprise a mobile HVAC, having an air flow path, an ion generator having a first housing and a second housing, the ion generator further comprising a first wire and a second wire extending from one of the first housing or the second housing, an end of each wire comprising a needlepoint brush, the mobile HVAC having a blower and motor, the ion generator being powered when the motor is operating the blower, and wherein each needlepoint brush extending into the air flow path.

In some optional embodiments, the following features may be utilized alone in combination with the ion generator or in combination with other features and the ion generator. The bipolar ionization system may further comprise a light on one of the first housing or the second housing to indicate power to the ion generator. The bipolar ionization system may further comprise grommets extending into a portion of the mobile HVAC and receiving the first wire and the second wire, respectively.

In still a further embodiment, a method of operating an ion generator, may comprise steps of providing a mobile HVAC with a blower motor and motor controller, electrically connecting the blower motor or the motor controller to a printed circuit board of the ion generator, converting an input power at the printed circuit board to an output for an ion generator module to create ions; and, positioning ion emitters in an airflow path of the mobile HVAC to introduce such ions into the airflow path.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. All of the above outlined features are to be understood as exemplary only and many more features and objectives of the various embodiments may be gleaned from the disclosure herein. Therefore, no limiting interpretation of this summary is to be understood without further reading of the entire specification, claims and drawings, included herewith. A more extensive presentation of features, details, utilities, and advantages of the present invention is provided in the following written description of various embodiments of the invention, illustrated in the accompanying drawings, and defined in the appended claims.

BRIEF DESCRIPTION OF THE DRAWINGS

In order that the embodiments may be better understood, embodiments of an ion generator will now be described by way of examples. These embodiments are not to limit the scope of the claims as other embodiments of an ion generator will become apparent to one having ordinary skill in the art upon reading the instant description. Non-limiting examples of the present embodiments are shown in figures wherein:

DETAILED DESCRIPTION

Figure 1:
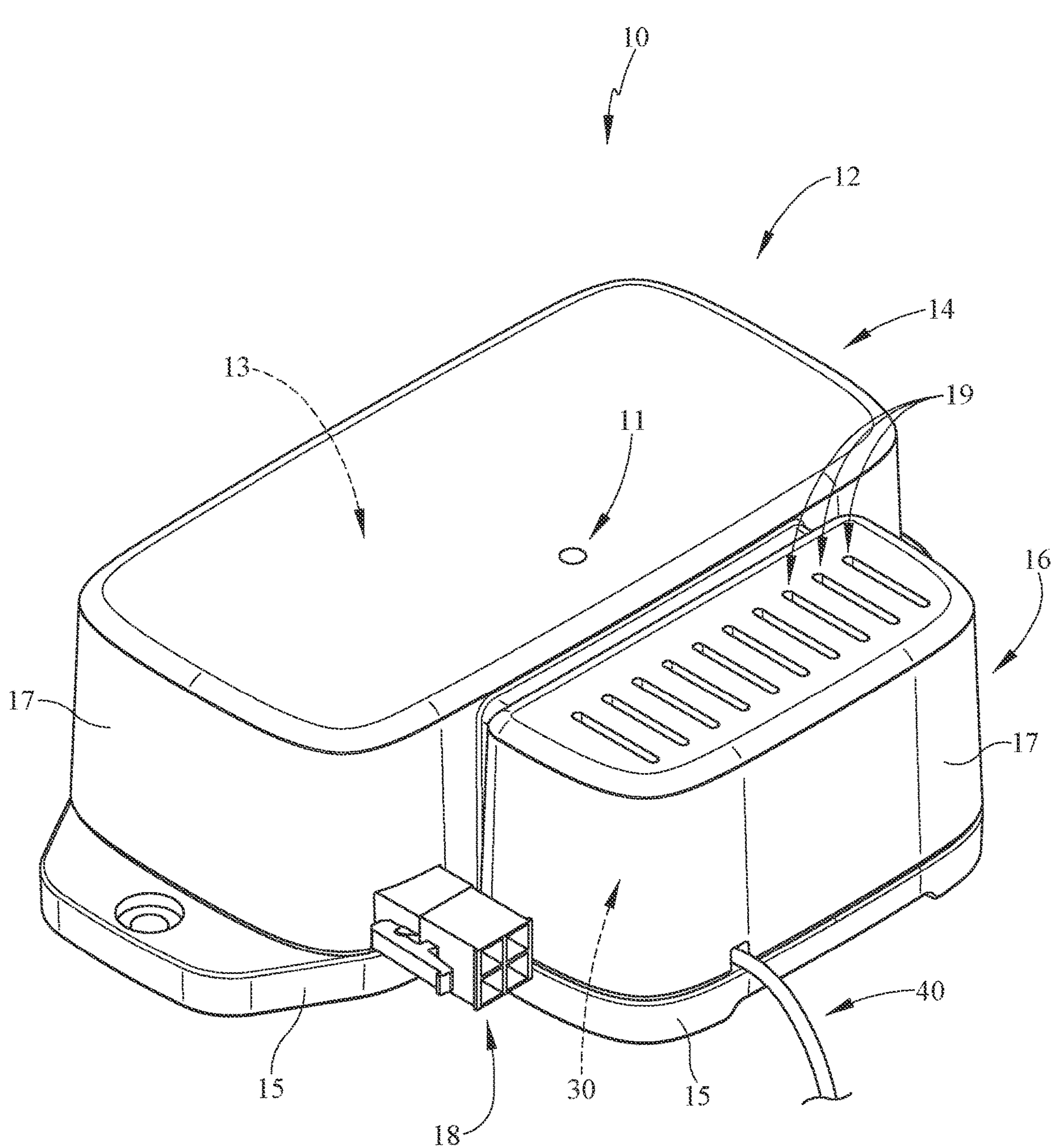
FIG. 1 is a perspective view of an example of a housing assembly for an ion generator.

It is to be understood that an ion generator is not limited in its application to the details of construction and the arrangement of components set forth in the following description or illustrated in the drawings. The described embodiments are capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings.

Reference throughout this specification to "one embodiment", "some embodiments" or "an embodiment" means that a particular feature, structure or characteristic described in connection with the embodiment is included in at least one embodiment of the present invention. Thus, appearances of the phrases "in one embodiment", "in some embodiments" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

The terms "air conditioner" or "air conditioning" will be used to encompass any treatment of air including heating and/or cooling HVAC systems. Air conditioning is also meant to encompass both indoor air conditioning, which is limited to the air conditioning of an enclosed area and outdoor air conditioning, which occurs in the open air.

Referring now to FIGS. 1-8, an ion generator and bipolar ionization systems are shown. The ion generator may be used with mobile HVAC systems, for non-limiting example RV and/or marine craft to define the bipolar ionization system.

Bi-polar ion generators raise the low voltage through the booster circuit (Ion Generator) to create a positive high voltage and create a negative high voltage. The positive high voltage and the negative high voltage creates high pressure ionized air (mainly oxygen) that generates a large amount of positive ions and negative ions. Simultaneous generation of positive ions and negative ions into the air generate a large energy release and the ions are attracted to the pathogens such as viruses. The ions break the hydrogen bond resulting in changes in the pathogens surface proteins, causing them to become inactive and effectively achieving sterilization. Additionally ion generators may charge particulate in order to cause particles to attract to one another and fall out of an airflow or to increase size and therefore increase effectiveness of a filter. Still further, the positive and negative ions may come into contact with organic volatile gas molecules (VOCs) and may break the chemical bonds of the VOC breaking such down into harmless compounds.

The ion generator may provide ionization of air flow moving through the mobile HVAC, on either side, positive or negative pressure, of the fan. The ion generator may be operable when the fan or blower of the HVAC operate to improve the efficiency and effectiveness of the ionization. The ion generator may be implemented in different manners depending on the type of mobile HVAC.

Referring now to FIG. 1, a perspective view of an example ion generator, or ionizer, 10 is provided. The ion generator 10 is shown with a housing assembly 12 having at least one housing 14. In the instant embodiment, the housing assembly 12 is shown having a first housing 14 and a second housing 16. The housings 14, 16 are shown connected together and may be integrally formed or may be formed and joined by fastener or adhesive. While two housing portions are shown, they may open to each other internally, or a single housing may be used. Additionally, in some embodiments, the housings 14, 16 may remain separated. In some embodiments, the housing assembly 12 may include a bottom 15 and a cover 17. Regardless of the number of housings and configuration, the housing assembly 12 may also include a cover or other accessibility feature so that the interior of the housing assembly is accessible for example during maintenance of the ion generator module 30 or a printed circuit board 13 therein. The housing assembly 12 may include some fastening structures which allow for connection of the housing assembly 12 to another fixed structure for mounting. In some embodiments, the ion generator 10 may alternatively, or additionally include, without limitation, adhesive, straps, hook-and-loop fasteners, clips, screws, or other mechanical fasteners, magnetic mounting, and/or mounting brackets or mounts affixed to, on, or through the housing assembly 12 or associated airflow path or HVAC system.

In some embodiments, the first housing 14 may house a power supply, defined in some embodiments on the printed circuit board 13 for power management, and the second housing 16 may include an ionizer module 30, which produces ions to introduction into the air flow path. For example, the printed circuit board 13 may function as a power converter or transformer for converting input power to the power required to operate the ion generator module 30. Additionally, as shown, the housing assembly 12 may include a light 11, for example a light emitting diode (LED), which indicates that the ion generator 10 is receiving power and/or indicate an operational status. This may be used to improve any installation, maintenance, or troubleshooting processes.

Figure 2:
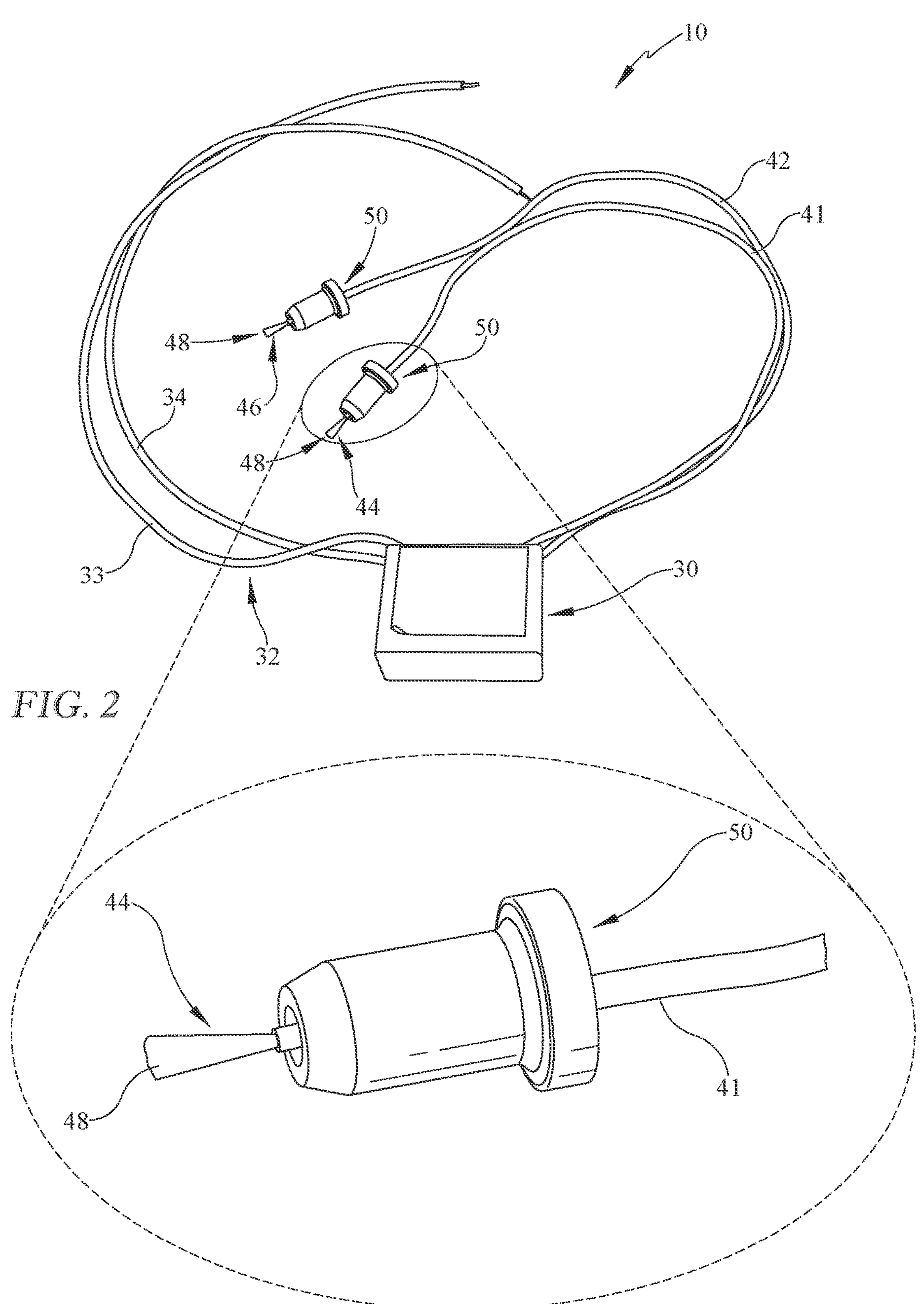
FIG. 2 is a perspective view of the of an example ion generator with housing assembly removed.

In some embodiments, the ion generator 10 may further comprise a first emitter wire 41 and a second emitter wire 42 (FIG. 2) extend from the housing assembly 12 and each define an emitter to introduce ions into an air flow path. For example, as shown in FIG. 2, the wires 41, 42 may be housed within the single cable 40 housing represented in FIG. 1. Alternatively, the first and second emitter wires 41, 42 may be separate wires as shown in FIG. 2, or as shown in FIG. 1, may be a cable having first and second wires or conductors housed therein. In such embodiment, the cable housing or sheath may be opened for splitting the internal wires or conductors. at or near a location of installation. In still further embodiments, two or more pairs of wires may be provided in two or more cables or by way of individual pairs of wires. Still further, in some embodiments, it may be desirable to eliminate the cable 40 or the emitter wires 41, 42 and place the emitters within the housing assembly 12. This may require one or more openings 19 in the housing assembly so that the ions can pass from within the housing assembly 12 into an airflow. These openings 19 are shown as slots in the embodiments, but various holes sizes, shapes, and arrangements may be utilized.

Also extending from the housing assembly 12 is at least one connector 18 for power. The connector 18 may receive a cable, or one or more wires, or a connector, from an HVAC, and more specifically in some embodiments from a power supply or controller for a blower motor so that the power of the fan or blower will power the ion generator 10. It may be desirable that the ion generator 10 only function when air flow is moving through the air flow path for improved ionization.

In operation the ion generator 10, and in particular the ion generator module 30 and emitters 44, 46 (FIG. 2) treat an airflow by discharge of bipolar ions to form an ionized air flow. The ionization may be positive and negative to charge the air flow and improve filtration of such.

Referring now to FIG. 2, a perspective view of the ion generator 10 is depicted removed from the housing assembly 12. The ion generator 10 comprises an ion generator module 30 with at least one power or control wire 32. In the instant embodiment, the at least one control wire is embodied by first and second power leads 33, 34 for example a positive and negative conductor or wire. The conductors may be rigid or flexible. The input to the ion generator module 30 may be 12V DC, for example. These wires 33, 34 may also be embodied by traces or other rigid structures within the housing assembly 12, for example the connector 18.

Additionally, extending from the ion generator module 30 are first and second emitter wires 41, 42. The emitter wires 41, 42 are embodied in the example as a positive and negative wire for corresponding positive and negative ions. For bipolar ionization, there may be one pair of emitter wires and emitters or there may be multiple pairs of wires and emitters. The ends of the emitter wires 41, 42 define emitters 44, 46, for example needlepoint emitters 48. The needlepoint emitters 48 may each be a single point emitter or may be multi-point emitters which may in some examples be brushes, metallic, tungsten, steel, or carbon fiber, for example. The emitters 44, 46 may be installed in a ducting or an air handler or some location where air flow moves and ions may be introduced to the air flow by the emitters located therein. The emitters 44, 46 may provide equal or differing amounts of ions, for example in some embodiments, the ion generator 10 may provide more negative ions than positive ions. The emitters 44, 46 may be external to the housing assembly 12 or may be internal as shown in FIG. 1.

In some embodiments, the emitter wires 41, 42 and emitters 44, 46 may pass through a grommet, or other retaining structure 50. During installation, the grommet 50 may be inserted into the air handler, the ducting or other location of air flow, in order to retain the exposed emitter 44, 46 in position for ion introduction to an air flow. In some other embodiments, a plate or other structure may be connected the air handler, ducting or other location, and the plate or other structure may be used to retain the emitters and wires.

In some embodiments, the emitter wires, or conductors 41, 42 may be embodied by rigid or flexible conductors and may be located exterior of the housing assembly 12 or may be interior to the housing assembly 12.

Figure 3:
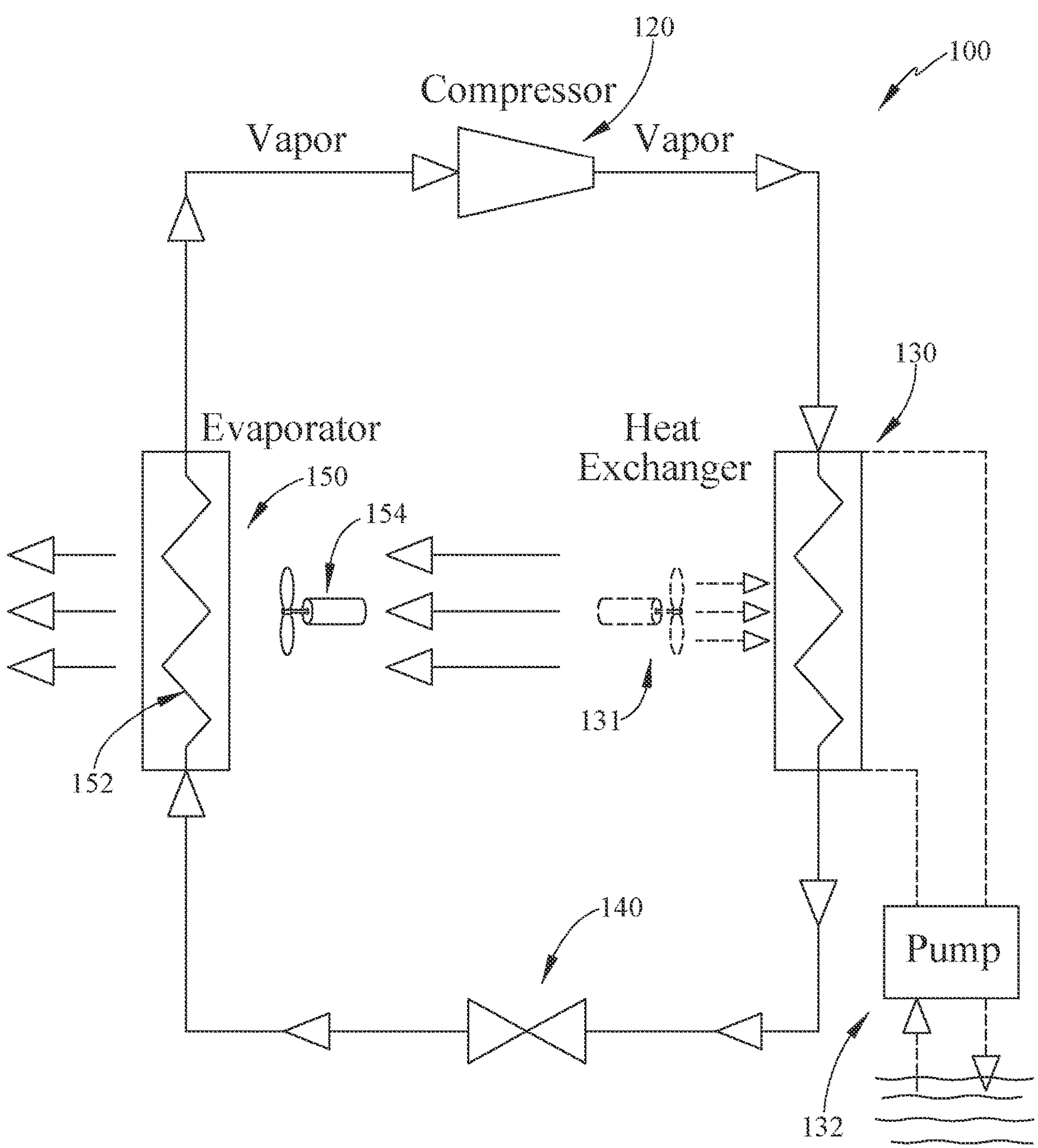
FIG. 3 is a schematic view of example cooling mechanicals which may be used in an HVAC.

The ion generator module 30 may include a module which defines an ionizer and provides ions to the emitter wires 41, 42 and to the emitters at the ends of the wires. Also within the housing assembly (FIG. 1), may be a circuit board 13 which receives power from, for example, a motor or motor controller for an HVAC fan or blower 154 (FIG. 3). In some other embodiments, it may be possible to power the ion generator 10, via circuit board 13, through a fan speed switch and/or unit power, for example from an air conditioning system or fan. The circuit board 13 may receive line power such as 115V-240V AC 50 or 60 HZ from direct or pulse width modulation, or DC power from a brushless DC blower motor controller direct or pulse width modulation signal, and convert such input power to a 12 V DC signal to power the ion generator module 30.

Referring now to FIG. 3, a schematic view of a plurality of cooling mechanicals used with an example air conditioning system, or HVAC 100. The term "cooling mechanicals" refers to the components that perform the conditioning of air, such as without limitation, a compressor, heat exchanger condenser, evaporator, and/or expansion device. Other components and devices may be utilized, and for example may include reversing valves for heat pump functionality or an electric heater. However, this list is not exhaustive but instead merely descriptive. Moreover, a heating function is not required with the air conditioning. The air conditioning system 100 is shown in schematic view for ease of discussion. As depicted, the compressor 120 compresses a refrigerant, which passes from the compressor 120 through the air conditioning system. The compressor 120 comprises a motor, which may be a part of the compressor structure or may be a separate components that connects to the compressor 120. The motor is not shown but generally represented and discussed as a portion of the compressor 120. In the circuit, the compressed refrigerant next passes through a heat exchanger 130, such as a condenser which cools the high pressure vapor into liquid refrigerant. The heat exchanger 130 which may be in the form of a condenser utilizing air cooling heat exchange with atmosphere, or in other embodiments may be water cooled condenser which exchanges heat with open water, such as a lake, river, sea, ocean, or the like. Further for example, in marine use, the condenser may be located within the air conditioning system or may be remotely located wherein the refrigeration conduit lines may extend to the cabin or other location where the remainder of the air conditioning system is located. The heat exchanger 130, when in the condenser form may include an optional fan 131 having a fan motor (both shown in broken line) to remove heat to atmosphere from the vapor passing through the coil. Alternatively, when in the form of a water cooled condenser, the heat exchanger 130 may provide a coil-in-coil heat exchange design in fluid connection with a pump 132 for open water and with fluid communication with a refrigerant line. The water cooled condenser may optionally include a titanium, or titanium alloy, portion of the coil to withstand use of open water such as rivers, lakes and salt water any of which may comprise abrasives.

Next, the refrigerant reaches a capillary tube 140, or in other embodiments an expansion valve 140, which reduces pressure of the liquid refrigerant, that then allows the refrigerant to boil and absorb heat as the refrigerant passes through an evaporator 150. The capillary tube, or expansion valve, meters the refrigerant moving from the heat exchanger 130 to the evaporator 150.

Figure 6:
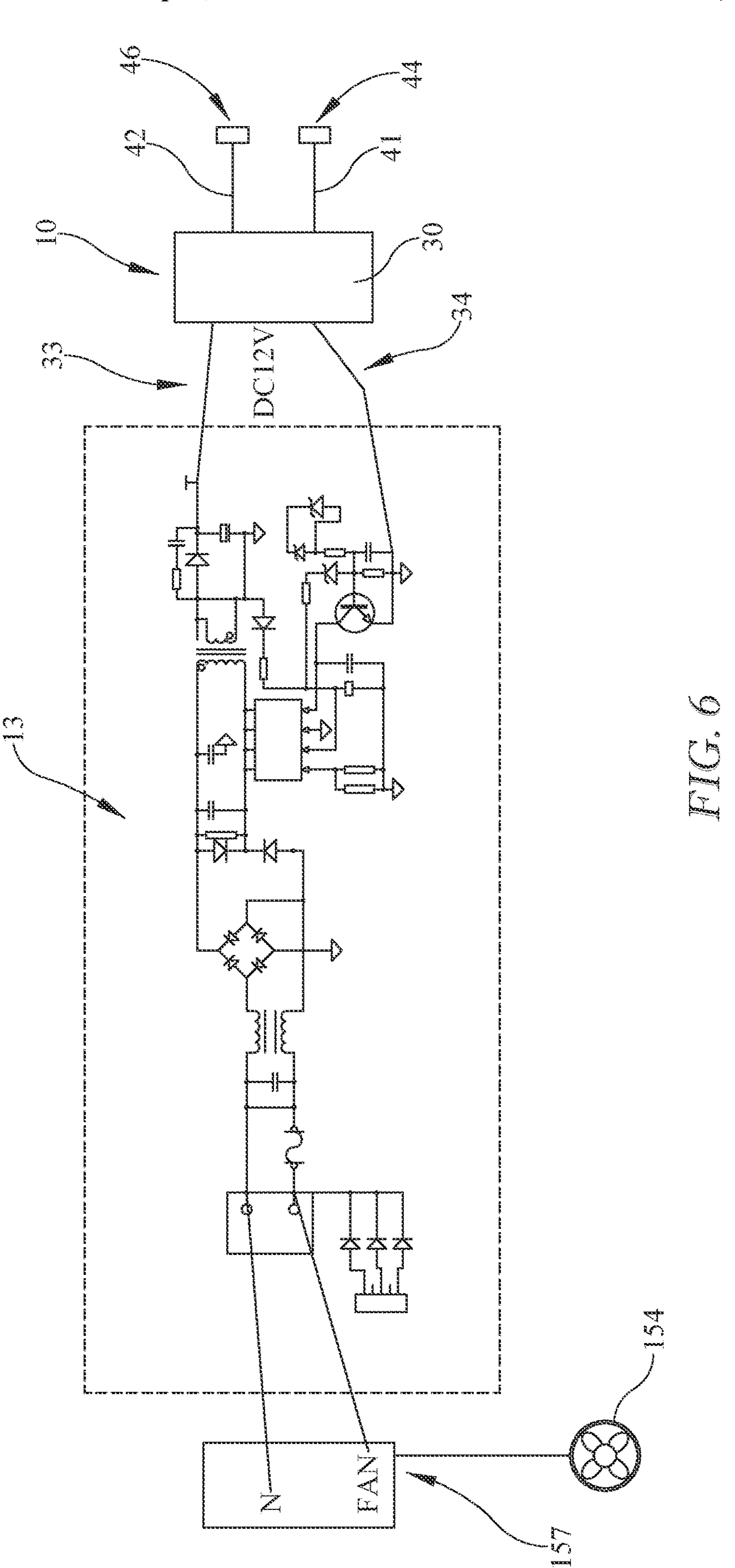
FIG. 6 is a schematic view of the electrical connection of the HVAC and the ion generator.
Figure 8:
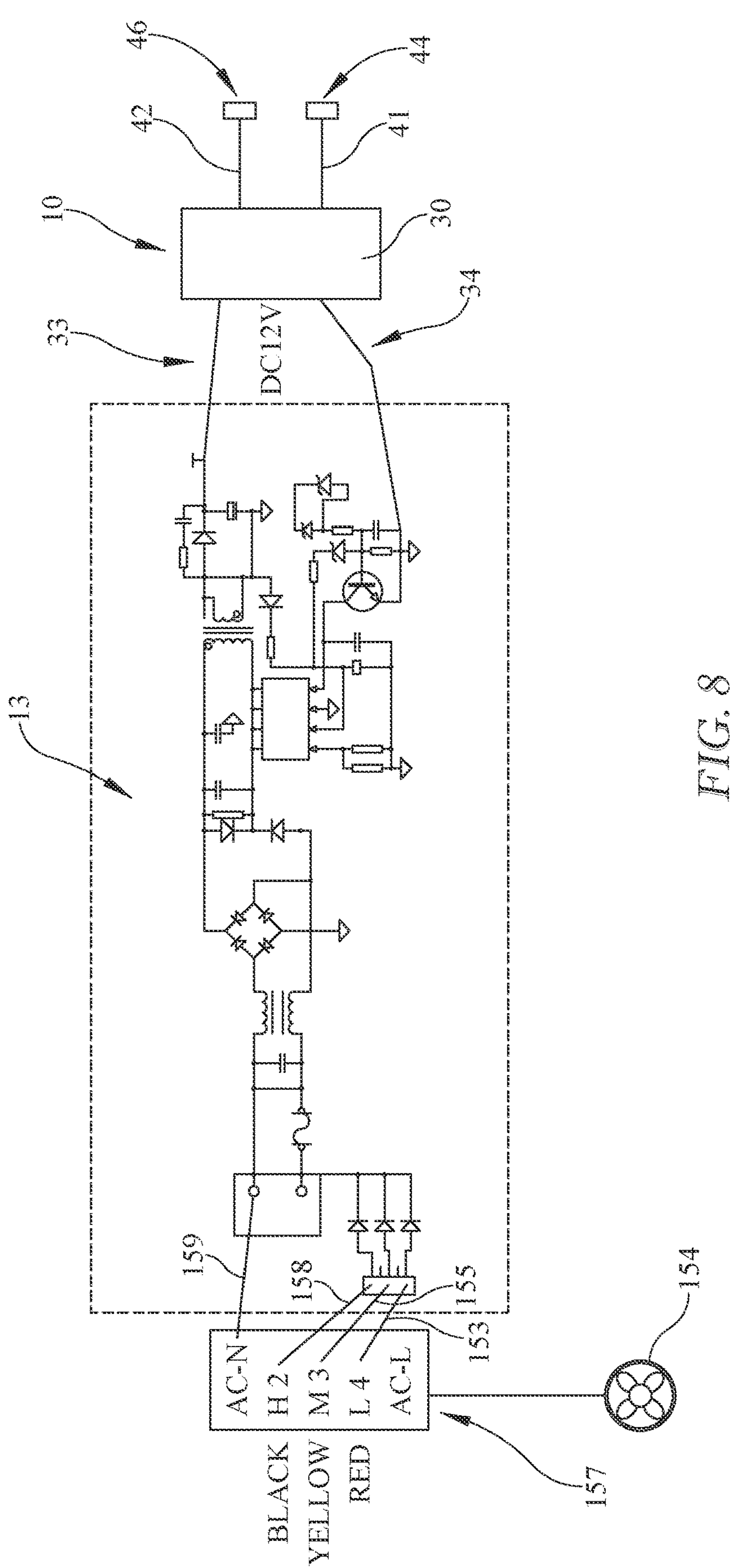

The evaporator 150 may have one or more coils 152 which extend in air flow communication with air flow directed to the room or zone so as to cool the area. It should be understood that the evaporator coils 152 may be in the room or zone, or the evaporator coils 152 may be remote from the room or zone wherein a duct servicing the room or zone delivers the conditioned air to the room or zone. A blower 154 is shown adjacent to the evaporator to create airflow through an airflow path. The blower or fan 154 may have various range of voltages and have a variable speed motor or distinct windings associated with varying speeds. The fan or blower motor associated with the blower 154 may be driven by a motor controller 157 (FIGS. 6, 8). The blower motor controller 157 may comprise various components including but not limited to a manual multi-position switch, a manual silicon controlled rectifier (SCR) control, or a digital/electronic Control. For example, a multi-position switch may be a device that is used with multi-tap motors where the position of the switch determines which tap is applied power and therefore what speed the motor runs. In another example, a manual SCR control may utilize a circuit of resistors, diodes, and potentiometer to control the amount of voltage applied to the motor thus determining speed. In this type of controller, varying the position of the potentiometer will vary the speed of the motor. This potentiometer may be embodied with a slide switch or a rotatory knob for non-limiting example. In still a further example, a digital/electronic control may be used. This type of controller comprises a digital input device, for example wall-mounted thermostat, a printed circuit board, mounted on or near the air conditioning unit. The printed circuit board may comprise various electronic components including, but not limited to, a triac that generates a pulse width modulation to the blower motor. The printed circuit board may also comprise a processor that receives input from the digital input device and then computes the frequency of the pulse thus determining the blower motor's speed. This input from the digital input device may be based on, for example, a temperature difference between room temperature and set point or it may be determined by a manual selection of fixed speed usually with a plurality of incremental steps, for example two to five steps.

After passing through the evaporator 150, the refrigerant returns to the compressor 120 for the compression to pass through the cycle again.

The refrigerant may be of various types. For example, some refrigerants which may be utilized include hydrofluorocarbons (HFCs), such as R-410A, HCFCs such as R-22, HFCs R-134a, R600a, R1234yf, and/or R1234e. Still further, newer refrigerants may include supercritical carbon dioxide, known as R-744, R-470a and R466a. These have similar efficiencies compared to existing CFC and HFC based compounds, and have lower global warming potential. These are merely examples however as other refrigerants may be used.

The schematic view is a simple compression cycle and other features and functions may be utilized. For example, additional conduit lines of further complexity may be utilized to provide the desired cooling. As previously mentioned, a reversing valve may be added to provide heat pump function. The schematic view, therefore, is merely exemplary for depicting the general refrigerant compression cooling cycle and should not be considered limiting, as other embodiments are possible.

Figure 4:
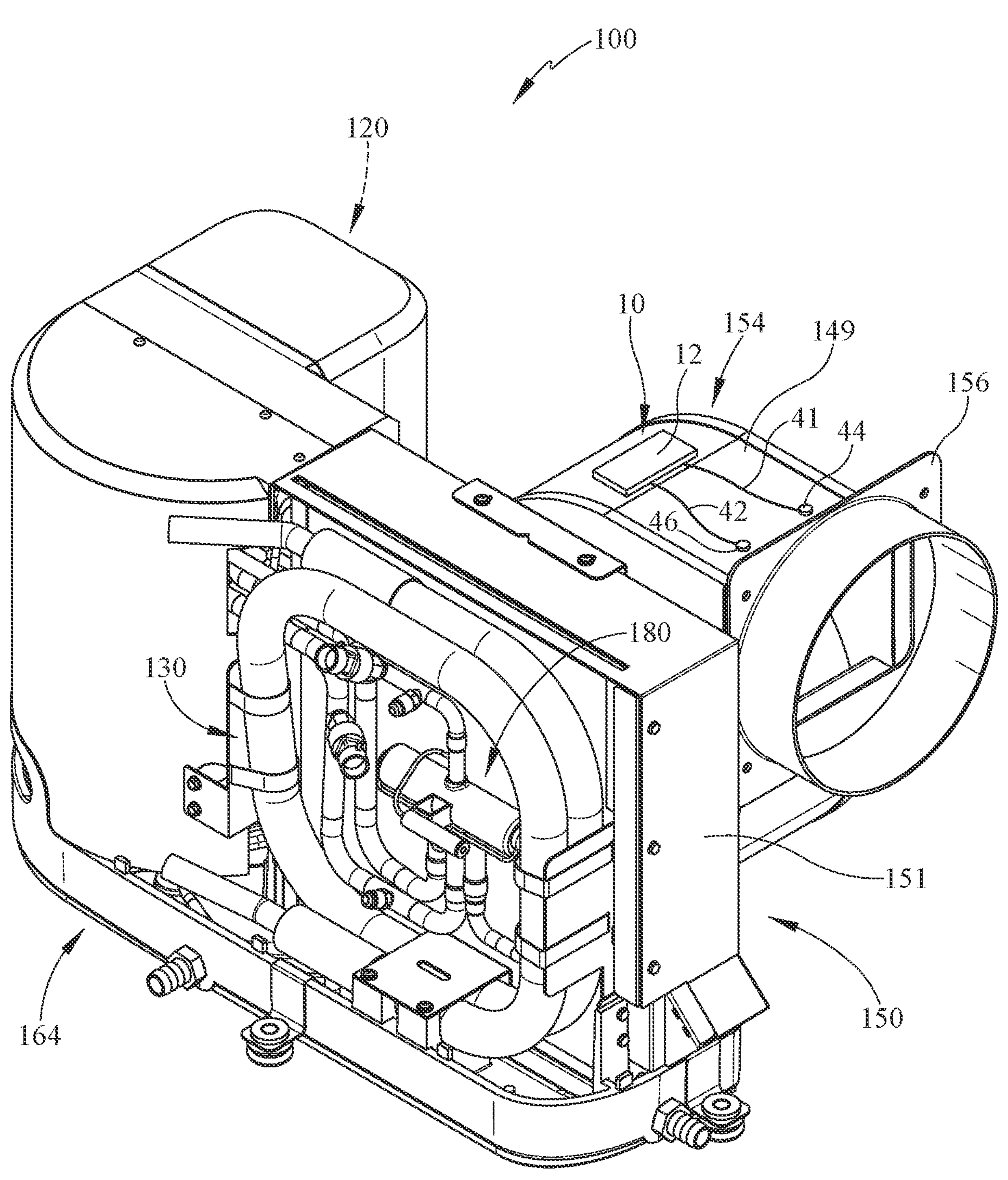
FIG. 4 is a perspective view of a mobile HVAC for a marine craft.

Referring now to FIG. 4, an example HVAC 100 is shown in perspective view. Moreover, the present embodiment is primarily designed for use in a marine craft or vehicle but as discussed further herein, obvious alterations are within the scope of the present disclosure and will have use in other applications such as conventional vehicles, recreational vehicles, aircrafts or other means of transportation and also in means of habitation. In this embodiment, the exterior of the air conditioner primarily comprises a drain pan or base pan 164, a blower 154, and a shroud structure composed of plurality of covers, some of which are removed for ease of understanding. The interior of the air conditioner primarily comprises a compressor 120 (inside a cover), a condenser 130, an evaporator 150 and a reversing valve 180.

Further, the air conditioning system 100 may include cooling mechanicals (FIG. 3) and in the marine embodiment may include an air or open-water cooled condenser for heat exchange of the refrigerant. In some embodiments, for example, the pumping system for the open water may be remotely located from the remainder of the mechanicals and the open water routed by conduit to the air conditioning system. The term open water refers to large open bodies of water such as lakes, rivers, seas, oceans, or the like. This may still be considered a self-contained system. Or, in other embodiments, one or more components, or cooling mechanicals, of any one air conditioning system may be located at differing locations.

In the instant embodiment, the compressor 120 may be an inverter compressor so that a corresponding compressor motor may be run at variable speed. The compressor 120 may include a motor integrally or may have a motor that is separate of the compressor structure but which drives the compressor structure. In some embodiments, the compressor 120 may be an inverter compressor and may therefore run at different speeds and may be more efficient than a single speed compressor. For example, when less cooling is needed, the inverter compressor may run at a lower speed, while at higher cooling loads, the compressor may run at higher speeds. When assembled, the compressor motor and compression component may be inside the first shroud or cover and the second shroud or cover.

Still further an evaporator shroud 151 may be provided which covers some or all of the evaporator 150. The shroud may comprise an air return opening to supply air to the evaporator, wherein in some examples the air return opening is in a face of the evaporator. The evaporator shroud 151 comprises a central opening in a sidewall, which is an inlet to the blower 154. The inlet is in fluid communication with air passing over the evaporator coil 152 so the conditioned air is next blown from the blower or fan 154. The blower 154 may have an additional blower shroud or housing surrounding the remainder of the structure. A blower outlet ring or flange 156 may be provided for connection to duct, which can guide the conditioned air to a desired location for dispersing in the RV or marine vehicle. The outlet ring 156 may be located at the blower outlet.

The ion generator 10 is shown on the housing 149 of the blower 154 in the example. However, the ion generator 10 (FIG. 4) may be located in various locations so that the emitters 44, 46 may be located anywhere in the air flow path of the mobile HVAC. While the emitters 44, 46 are shown at the blower housing 149, the emitters may be located in other locations, such as at the evaporator 150 near the blower inlet. Various locations may be utilized for the emitters, and the housing assembly may be located in various locations, dependent on the space available around the mobile HVAC which is often limited in marine applications.

Figure 5:
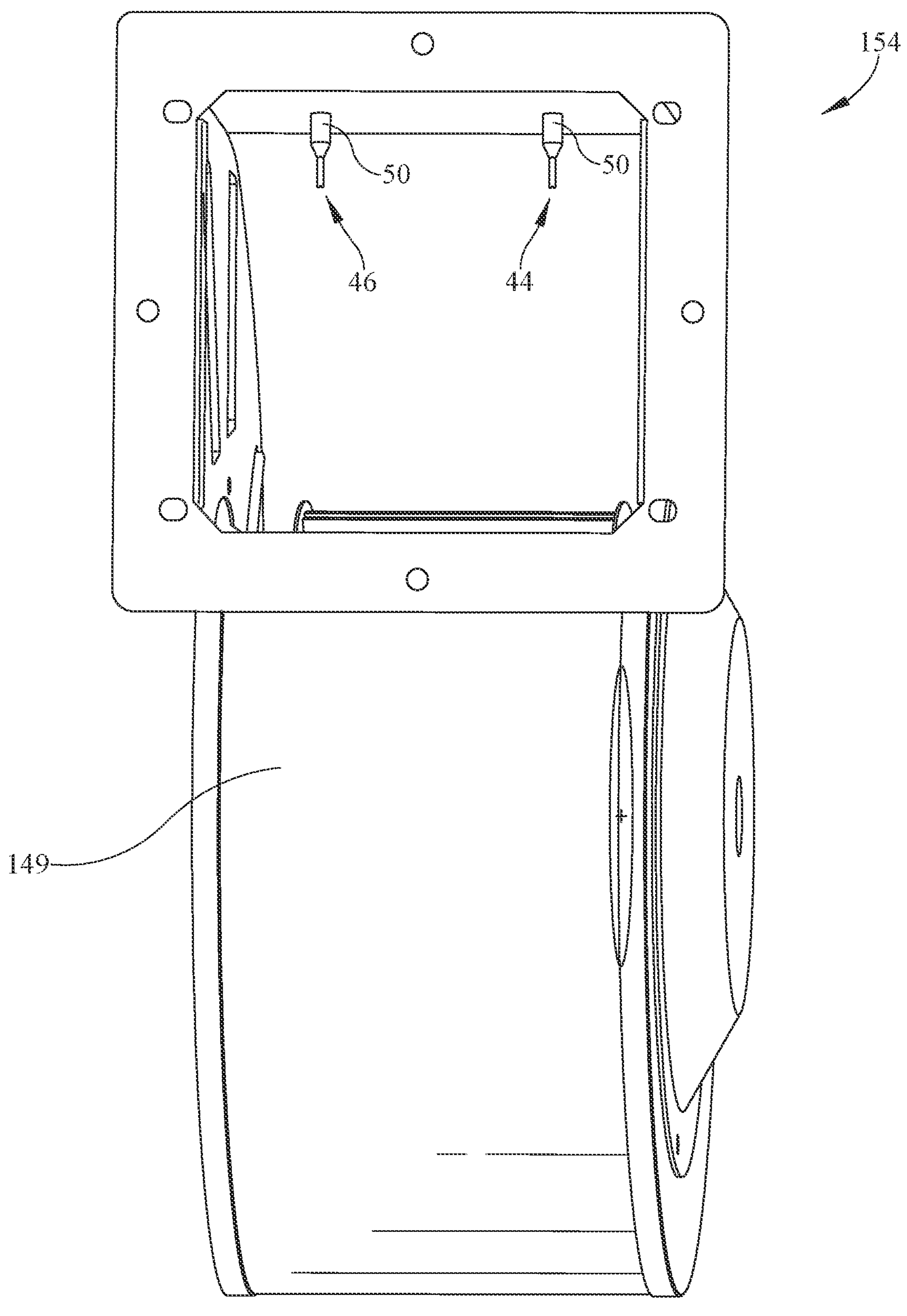
FIG. 5 is a perspective view of an example mounting configuration for emitters in an air flow path, for example the blower housing of FIG. 4.

Referring to FIG. 5, an elevation view of the blower 154 is shown. The emitters 44, 46 are shown located within the blower housing 149 so as to introduce ions to the air flow path. The emitters 44, 46 are shown a distance apart. In some instances, the distance may be from about one inch to several feet spaced apart. The ion generator 10 (FIG. 1) may be mounted on the blower housing or elsewhere in the HVAC, or alternatively may be remotely located.

Referring now to FIG. 6, a schematic wire diagram of the bipolar ionization system is shown for use in the marine embodiment. The fan 154 of the marine system is shown on the left side of the drawing is electrically connected to an electronic motor controller 157. The motor controller 157 provides power, for example 115V to 240 V AC at 50 or 60 Hz, or alternatively may be a DC power input for example from 280 V to 420 V DC which may or may not be pulse width modulated, to the printed circuit board 13 of the ion generator 10 and within the housing assembly 12. The motor controller 157 converts an input from the electronics of a digital thermostat and outputs a varying voltage, constant voltage, PWM, and/or BLDC motor output. The controller 157 also converts the input from the digital thermostat to start up the blower motor and/or control the speed of the motor. The controller 157 may be a mechanical device which for example functions as a switch and activates the blower motor windings, for example three corresponding to low, medium, and high speeds. The controller 157 may be an electronic device, which, for example, activates 3 separate relays for speeds when using a digital thermostat to control the speeds. In some other embodiments, the motor controller 157 may provide DC power output to the printed circuit board 13. In some embodiments, the printed circuit board 13 may receive power output from the motor control 157 a pulse width modulation (PWM) to convert the varying pulse width frequency and/or voltage constant or varying input to a constant 12 V DC output for the ion generator module 30. The marine fan 154, in some embodiments may be a variable speed fan and therefore have a single output from the motor controller 157 to the printed circuit board 13. The printed circuit board 13 may then convert the input power to a 12 V DC power to operate the ion generator 10. The 12 VDC input power to the ion generator module 30 is represented by a first wire 33 (FIG. 2) and a second wire 34 (FIG. 2), wherein one wire represents a positive and the other wire represents a negative. The wires 33, 34 electrically connect to the printed circuit board 13 therein. The printed circuit board 13 may receive direct voltage, pulse voltage (PWM), or varying voltage to convert to a power output for the ion generator 10. The printed circuit board 13 changes the input power, for example from 115V AC to 12 DC output to power the ion generator 10 and introduce ions by way of the ion emitters 44, 46. The ion generator 10 is in electrical communication with the printed circuit board 13 and receives power therefrom, when the fan or blower 154 is operating. The ion generator 10 may then create ions and introduce them to the air flow by way of the ion emitters 44, 46.

Figure 7:
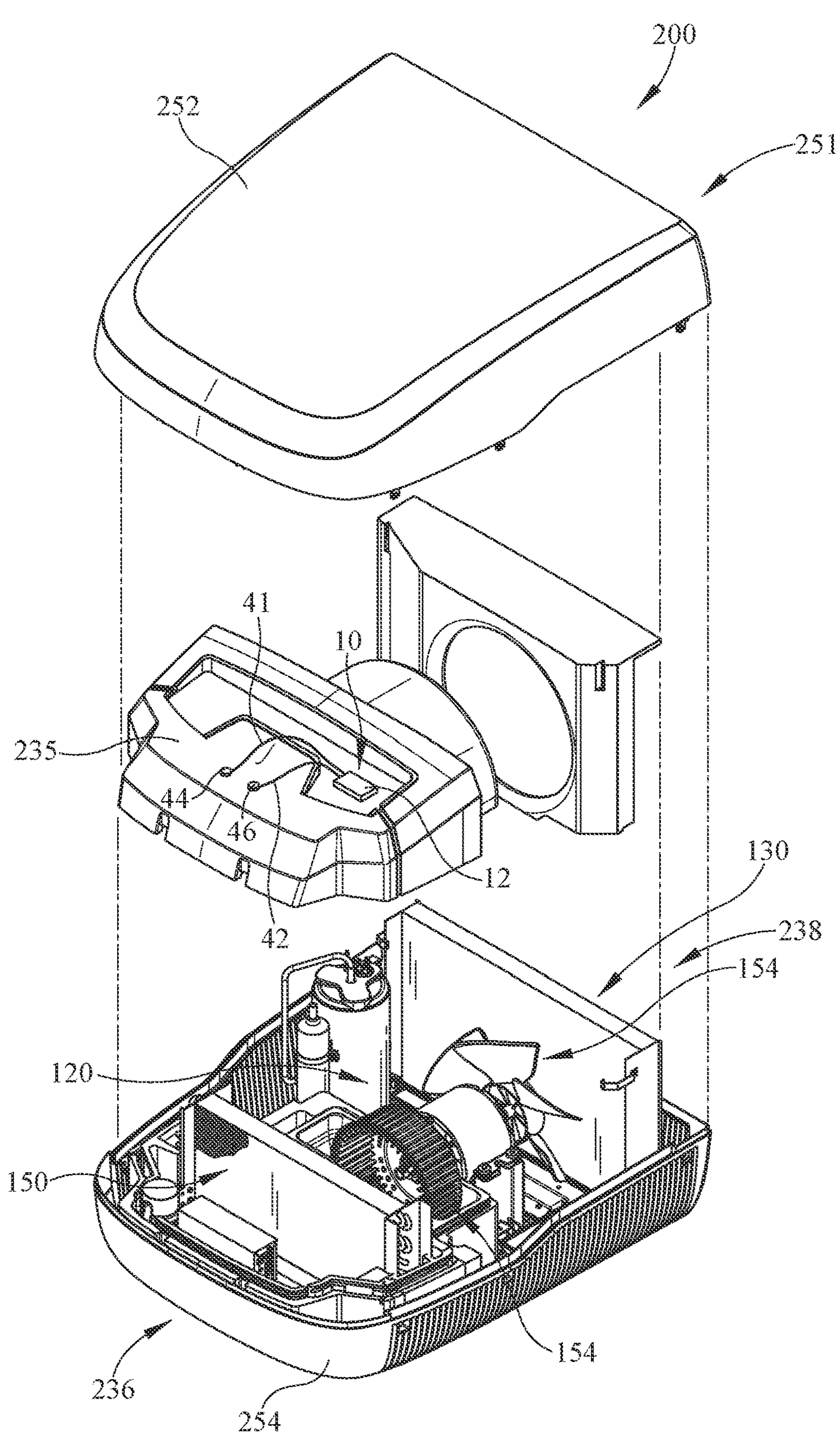
FIG. 7 is an exploded perspective view a mobile HVAC for a recreational vehicle; and, FIG. 8 is schematic view of the electrical connection of the HVAC of FIG. 7 and the ion generator.

Referring now to FIG. 7, an exploded perspective view of an HVAC 200 for a recreational vehicle (RV) is depicted. As used herein, the term "recreational vehicle" (RV) refers to mobile homes, motor homes, travel trailers, fifth wheels, recreational vans and the like. A recreational vehicle may be one type of mobile unit. It should also be understood by one skilled in the art that the instant embodiment may be utilized with stationary structures having roof-mounted air conditioning units and air conditioning ducts extending through the ceiling area of the structure. Alternatively however, the RV may be in the form of a non-powered, pull-behind camper, non-mobile structures, and watercraft. For example, the embodiments of the instant disclosure are also suitable for use in various water crafts having exterior air conditioning units and duct work passing through cavities or spaces between the roof and ceiling.

The HVAC 200 is shown removed from a recreational vehicle (RV) and may be include the mechanicals of the HVAC 100 shown in FIG. 3. The mobile AC or HVAC unit 200 comprises a housing 251 which may be mounted on the exterior of the RV. As with previous embodiments, the housing 251 may be located, for non-limiting example, on the roof, a rear wall, or other location of an RV. The housing 251 may comprise a forward end 236, toward the left side of the depicted figure, and a rearward end 238 toward the right side of the depicted figure, and sides extending between the forward and rearward ends 236, 238. The forward and rear ends 236, 238, may be defined, for example, by the forward and rearward directions of the RV but this is merely descriptive and should not be considered a limiting characteristic. The housing 251 may be formed of various shapes and in some embodiments, may have a curved or aerodynamic characteristics desirable to improve fuel mileage and approve aesthetic appearance. The housing 251 may be formed of a one-piece enclosure or may be formed of multiple structures to define the enclosure. For example, the present housing 251 may be formed of a base pan 254 and a shroud 252 positioned over the top of the base pan 254. The parts of the housing 251 may be entirely separable or may be hinged, for example in a clam shell-like arrangement. Each of the air shroud 252 and the base pan 254 may include sidewalls which meet to form a seam.

Within the RV HVAC 200 may be the compressor 120, the condenser 130, the evaporator 150 and blower or fan 154. The condenser 130 may also include a fan to exchange heat to atmosphere, when the fan 154 is operating.

A foam insulation 235 may also be located over the evaporator 150 to create an airflow path between the RV and the HVAC 200. In other embodiments, a metal or plastic may be positioned over the evaporator in order to form an enclosure defining at least a portion of an air flow path. The emitter wires 41, 42 and emitters 44, 46 may be inserted into the foam insulation enclosure 235, or other enclosure material and therefore into the airflow path. In still further embodiments, the emitters 44, 46 may be located in other locations of the air flow path. This may be on either the positive pressure or negative pressure side of the fan 154. In either event, the emitters 44, 46 may introduce ions to the air flow providing charging of the air for better cleaning and filtration.

Referring still to FIG. 7, the housing 251 is again shown wherein the air shroud 252 is exploded from the base pan 254. Within the base pan 254 are a plurality of cooling mechanicals, or cooling components, which may also include one or more heating structures, for example a heating element. Still further, other heating components may be located within the housing, for example a furnace or heat pump arrangement may be utilized to provide heat throughout the RV. The depicted base pan 254 shows a condenser 130 at the rear end 238 of the base pan 254 and a foam insulation 235 at the forward end 236 of the base pan 254. Beneath the foam insulation 235 at the forward end 236 of the base pan 254 may be the evaporator 150 and fan 154 to push air from the interior space of the RV through the evaporator 150 for heat exchange and force the air back into the RV. As one skilled in the art will understand, the condenser 130 also functions as a heat exchanger pulling air across a plurality of coils to exchange heat with the ambient air pulled into and blown out of the housing. The fan 154 for the cooling mechanicals may comprise one or more fans which are utilized with the evaporator 150 and the condenser 130 for the heat exchange described. In the instant embodiment for example, there may be two fans, one for the evaporator 150 and one for the condenser 130. There may be a single motor or two motors for these fans.

Referring now to FIG. 8, a schematic view of a wiring diagram of for an RV HVAC 200 of FIG. 7. The fan or blower motor 154 of the HVAC unit is shown comprising 3 wires 153, 155, 158 and a neutral wire 159. These wires 153, 155, 158, 159 are shown connected to the electronic motor controller 157. The three wires 153, 155, and 158 each correspond to one speed or motor winding, for example low, medium, and high speeds of the fan 154. In some embodiments, the wires 153, 155, 158 may be connected to a multi-speed fan switch. In such embodiment, the switch may be mechanical or electronic. The wires are inputs to the housing assembly 12, and more specifically the printed circuit board 13 within the housing assembly 12. The printed circuit board 13 changes the power input from the fan motor, for example 115V AC at 60 HZ to a 12V DC input for the ion generator 10.

It should be understood by one skilled in the art that while the configurations of FIGS. 6 and 8 are describe as related to marine and RV use respectively, that either arrangement is capable of being used with the other of marine or RV use, or altered for use with the other of marine or RV. For example, the system of FIG. 6 may be installed in an RV with a brushless DC blower motor and/or motor controller with pulse width modulation, in order to utilize such within an RV environment. Variations of this or other types of changes in configuration may be utilized and therefore the description of use with RV or marine should not be considered limiting.

Present embodiments provide an ion generator and a system comprising an ion generator and an HVAC and a method of operating the ion generator. The HVAC may be a fan alone in some embodiments so long as an air flow path is induced and a power line or signal from the fan motor or a fan motor controller may be in electrical communication to power the ion generator 10.

All definitions, as defined and used herein, should be understood to control over dictionary definitions, definitions in documents incorporated by reference, and/or ordinary meanings of the defined terms. The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases.

Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures.

The foregoing description of methods and embodiments has been presented for purposes of illustration. It is not intended to be exhaustive or to limit the invention to the precise steps and/or forms disclosed, and obviously many modifications and variations are possible in light of the above teaching. It is intended that the scope of the invention and all equivalents be defined by the claims appended hereto.

The invention claimed is:

1. An ion generator, comprising:

a housing assembly having a first housing and a second housing, said housing assembly configured to be mounted on an exterior of a blower of a mobile HVAC, said first housing and said second housing each having an interior volume;

a first wire extending from said housing assembly and a second wire extending from said housing assembly;

a circuit board in one of the first housing or the second housing, said circuit board receiving a high voltage AC and converting to a lower voltage DC;

a potted ion generator module in the other of the first housing or the second housing to create ions and in electrical communication with said first wire and said second wire;

a first end of a first grommet receiving said first wire and a first end of a second grommet receiving said second wire;

a first emitter at an end of said first wire and a second emitter at an end of said second wire, each of said ends having a brush, said first emitter extending from a second end of said first grommet and said second emitter extending from a second end of said second grommet, wherein said first grommet and said second grommet are spaced away from said housing assembly; and, further comprising a quick-disconnect connector which extends from the housing assembly, said quick-disconnect connector capable of receiving power from a blower motor controller of said mobile HVAC so that said ion generator operates when one of a blower motor or said blower motor controller is operating.

2. The ion generator of claim 1, said first wire and said second wire extending through each of said first and second grommets, respectively.

3. The ion generator of claim 2, said mobile HVAC being a marine HVAC system.

4. The ion generator of claim 3, said marine HVAC system comprising a blower housing.

5. The ion generator of claim 4, said blower housing having first and second holes capable of receiving the first and second grommets respectively of the first wire and the second wire.

6. The ion generator of claim 3, said circuit board configured to receive a power input from said blower motor controller and outputs DC power to said ion generator.

7. The ion generator of claim 2, said mobile HVAC being a recreational vehicle (RV) HVAC system.

8. The ion generator of claim 7, said RV HVAC system having an enclosure.

9. The ion generator of claim 8, said first and second grommets and said first wire and said second wire disposed in said enclosure.

10. The ion generator of claim 7, said circuit board configured to receive a power input from said blower motor controller and outputs DC power to said ion generator.

11. The ion generator of claim 1, further comprising a light to indicate power on said housing assembly.

12. An ion generator, comprising:

a housing assembly comprising a first housing, a second housing, a bottom, and at least one cover, said housing assembly positioned on an exterior of an HVAC blower housing or a duct, or remotely from said blower housing;

an ion generator module and a circuit board potted within said housing assembly, so that said ion generator and said circuit board are self-contained within said housing assembly;

first and second wires extending from said housing assembly, a first end of said first and second wires coupled to said ion generator;

a first grommet and a second grommet, a first end of said first grommet receiving said first wire, and a first end of said second grommet receiving said second wire;

a second end of said first and second wires each comprising a pin or a brush to emit ions, said pin or brush of said first wire and said second wire extending from said second ends of said grommets, respectively;

said grommets and said pin or brush spaced from said housing assembly and passing through an external surface of said blower housing or said duct;

a quick-disconnect connector on an exterior of said housing assembly and capable of providing power to said circuit board within said housing assembly from a blower motor or blower motor controller.

13. The ion generator of claim 12, said housing assembly having a plurality of vent apertures.

14. The ion generator of claim 12, one of said first housing and said second housing being larger, and said larger housing having said circuit board therein.

15. The ion generator of claim 14, the other of said first and second housing being smaller, and said smaller housing having said potted ion generator module therein.

* * * * *